United States Patent [19]

Moran et al.

[11] Patent Number: 4,776,340
[45] Date of Patent: Oct. 11, 1988

[54] HEMATOCRIT MEASUREMENT BY DIFFERENTIAL OPTICAL GEOMETRY IN A SHORT-TERM DIAGNOSTIC CARDIOVASCULAR CATHETER, AND APPLICATION TO CORRECTION OF BLOOD-OXYGEN MEASUREMENT

[75] Inventors: Byron L. Moran, Santa Barbara; Allan F. Willis, Newbury Park, both of Calif.; Yitzhak Mendelson, Worcester, Mass.

[73] Assignee: Spectramed, Inc., Oxnard, Calif.

[21] Appl. No.: 28,756

[22] Filed: Mar. 23, 1987

[51] Int. Cl.$^4$ .............................................. A61B 5/00
[52] U.S. Cl. .................................................. 128/634
[58] Field of Search ............... 128/634, 696, 633, 362, 128/395, 665, 396, 397, 398; 356/241, 39, 41, 40; 350/96.26

[56] References Cited

U.S. PATENT DOCUMENTS 4,623,248  11/1986  Sperinde ............................ 128/634

OTHER PUBLICATIONS

Spectrophotometric Monitoring of Arterial Oxygen Saturation in the Fingertip by Yoshiya, Shimada, Tanaka in Medical & Bio. Eng. & Computing Jan. 1980.

Primary Examiner—William E. Kamm
Assistant Examiner—George Manuel
Attorney, Agent, or Firm—Ashen Golant Martin & Seldon

[57] ABSTRACT

An optical fiber carries a light beam through a cardiovascular catheter and projects the beam into the patient's bloodstream. Two other fibers, spaced in a very carefully controlled configuration from the first, receive light scattered by corpuscles (and blood-vessel walls) and transmit this reflected light back through the catheter to respective detectors outside the patient's body. If preferred, two input fibers and a single output fiber—or other techniques for providing differential geometry—may be used instead. Electronic instrumentation finds the ratio of the two light fluxes, thus cancelling out unknown variables such as input light intensity and optical—connector attenuation. The known differential geometry between the two light paths permits calibration of the ratio measurement in terms of corpuscular concentration—i.e., hematocrit. Light at only one wavelength suffices for the measurement. Advanced forms of the invention correct for proximity of blood-vessel walls. This system is particularly compatible with optical-fiber measurements of oxygen saturation, as either or both of the light paths already provided may be used for the oxygen reflectometry.

16 Claims, 7 Drawing Sheets

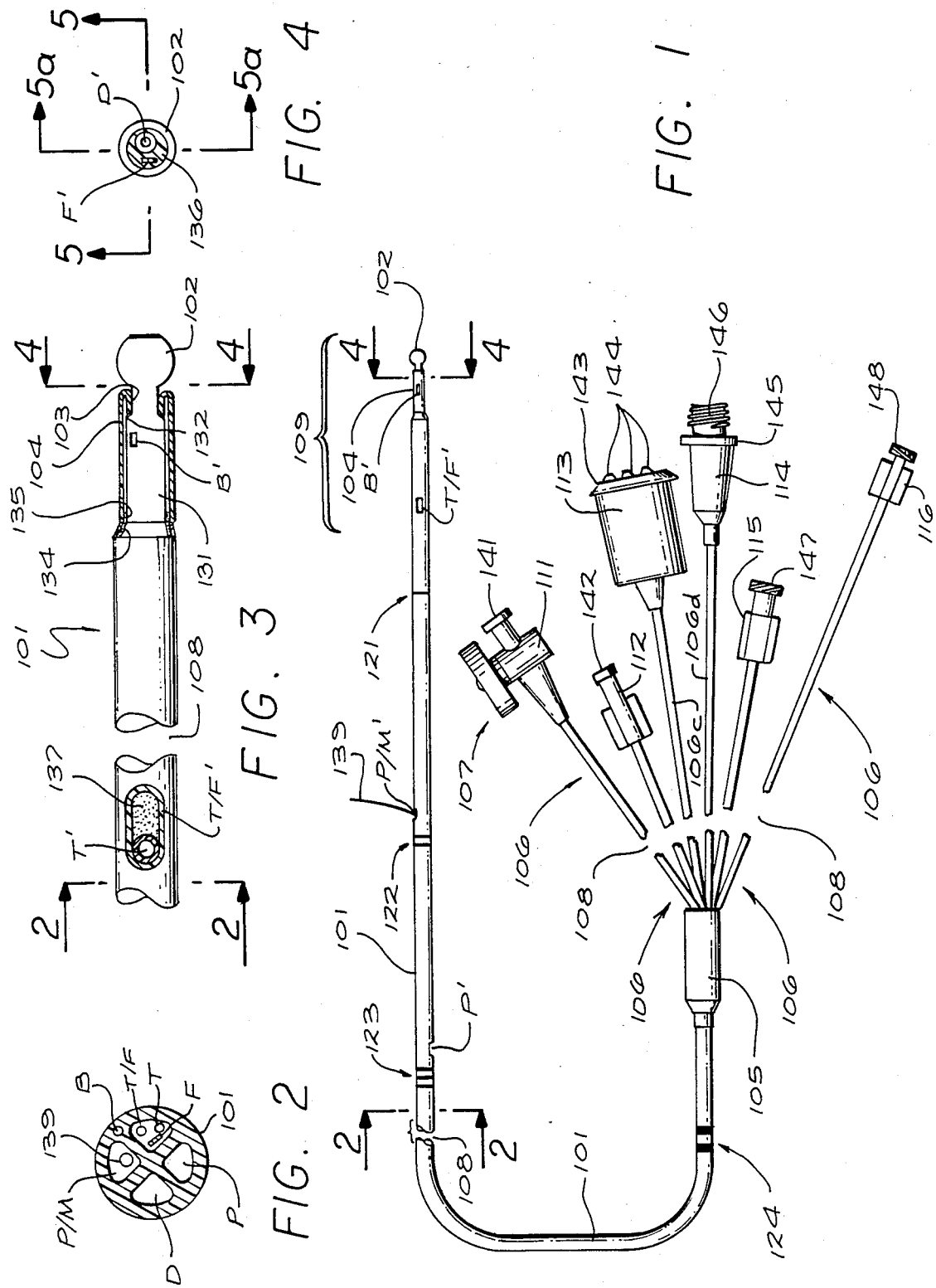

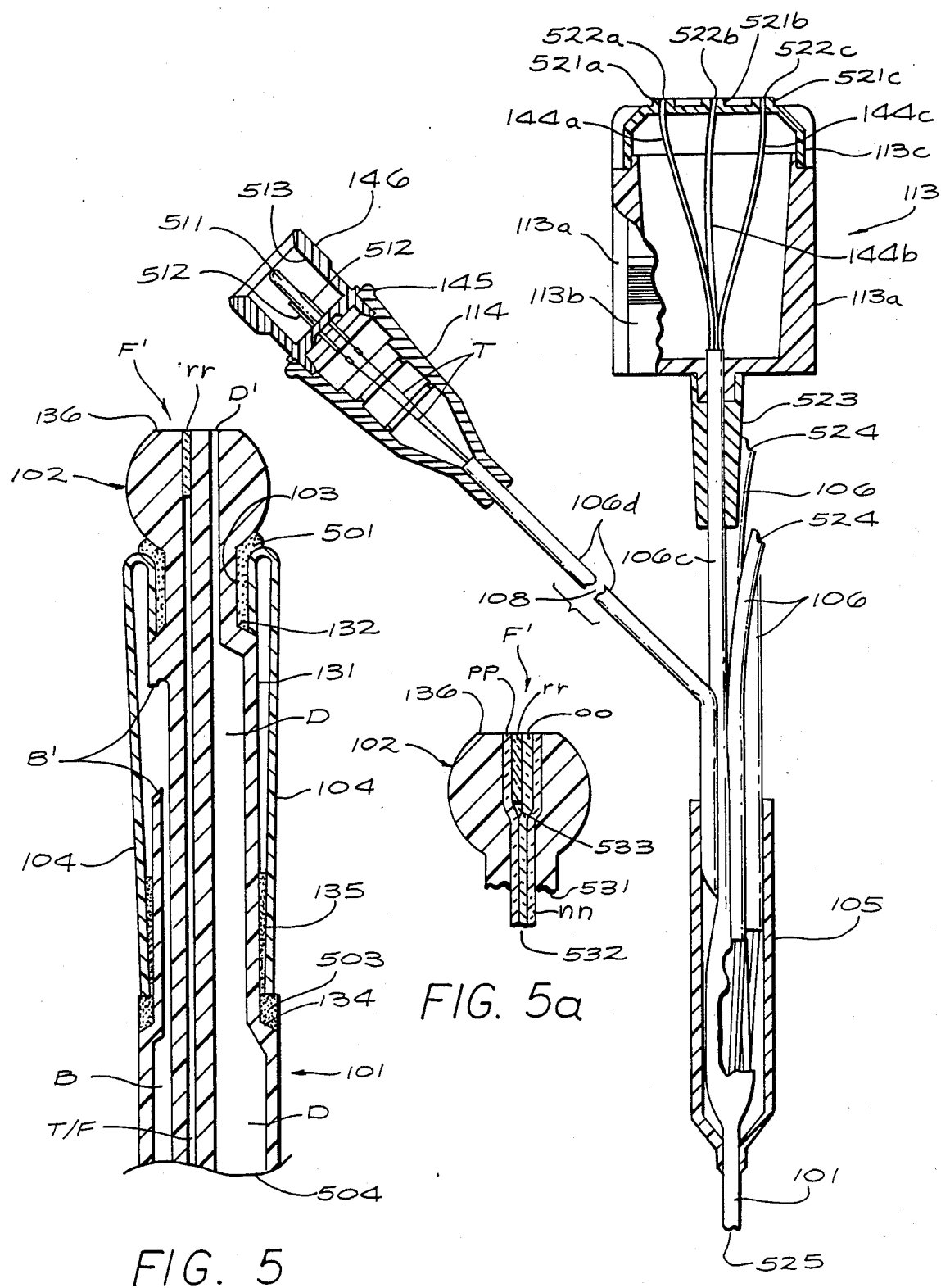

HEMATOCRIT MEASUREMENT BY DIFFERENTIAL OPTICAL GEOMETRY IN A SHORT-TERM DIAGNOSTIC CARDIOVASCULAR CATHETER, AND APPLICATION TO CORRECTION OF BLOOD-OXYGEN MEASUREMENT

BACKGROUND

1. Field of the Invention

This invention relates generally to optical catheter systems used for measuring properties of materials in suspension in fluids. It relates more particularly to diagnostic cardiovascular catheters which are used for short-term diagnoses, and which include optic fibers—whose polished tips are immersed in a patient's bloodstream —for reflectometric assays of blood characteristics.

For such measurements the tips of the optic fibers are usually positioned in the patient's right ventricle or pulmonary artery. At those locations nearly all the blood circulating in the body is collected and well mixed for return to the lungs. Consequently the conditions (such as oxygen-saturation level) there represent by definition a good average of venous conditions for the whole body.

By "short term" we mean brief periods such as minutes or hours. Much longer usages, such as months or years, characterize a very different type of device—a so-called "permanent" implant, often part of a pacemaker system.

2. Prior Art

Our invention has application in a great variety of fields. We are familiar with relevant prior art, however, only in the area of cardiovascular diagnostic catheters.

Cardiovascular catheters that include optic fibers are well known for short-term measurement of blood-oxygen saturation. Notable U.S. Pat. Nos. in this area are 4,295,470, 4,114,604 and 3,847,483 to Shaw et al., and 4,523,279 and 4,453,218 to Sperinde et al. These systems generally project light of two or three different wavelengths into the blood.

In general the blood differentially reflects the light components of different wavelengths, and the difference—or preferably the ratio—of reflectances varies with the level of oxygen saturation in the blood. Consequently the reflectance ratio can be used as a measure of oxygen saturation.

Such systems using just two wavelengths are subject to systematic measurement inaccuracies. As noted in the aforementioned Shaw U.S. Pat. No. 4,114,604, hematocrit (loosely speaking, the concentration of blood corpuscles in the blood) is among several factors that "introduce errors into the oxygen saturation measurements" made using two wavelengths.

Shaw resolves this and other uncontrolled influences by introducing and detecting light of a third wavelength: this technique provides enough information to correct the oxygen measurement for the unknown effects. Such a refinement is of course very useful, but relatively cumbersome in requiring three different light sources.

Moreover, at least in the form proposed by Shaw it only corrects for the effects of hematocrit without actually providing a usable measurement of hematocrit itself. This limitation is regrettable since hematocrit does have independent diagnostic significance.

Another area of prior research that may be relevant to the present field is represented by the paper "Implantable Telemetry for Measurement of $O_2$ Saturation," due to J. M. Schmitt, F. G. Mihm, J. Shott and J. D. Meindl. Their article appeared in *IEEE Frontiers of Engineering and Computing in Health Care* at page 703 (1984).

This paper of Schmitt et al. is in a somewhat different subfield from the present invention, as it relates to long-term measurement of oxygen saturation and teaches away from the use of optic fibers.

The Schmitt et al. system incorporates implantable transducers positioned directly at the measurement site, within the patient's body. There is no optic fiber; rather, any necessary light source(s) and detector(s) are exposed directly to the patient's bloodstream. The system does measure both oxygen concentration and hematocrit.

The paper also suggests that the ratio of intensities detected at two different source/detector distances might be used to determine hematocrit, independent of oxygen saturation. The paper discloses no particular configuration for doing so.

In principle, data can be extracted from the Schmitt system (and from the patient's body) by radio telemetry to diagnostic instruments in the laboratory. In view of certain stringent limitations, however, the only useful applications of the Schmitt system would appear to be in implanted control systems for pacemakers.

Specifically, the Schmitt system has the disadvantages of very extreme costliness and fragility. Production and assembly techniques for such devices, as described by Schmitt et al., are extremely awkward and difficult.

In order to attain reasonable operational stability and reliability, the Schmitt group found it necessary to assemble the various elements of their device (including an integrated-circuit controller) on a silicon wafer, and then to encapsulate it. As will readily be appreciated by those skilled in the art, such procedures are among the most demanding and expensive of all industrial techniques.

The finished Schmitt device is an elaborate wafer-mounted transducer array, hermetically sealed with solder connections and so forth. Each optical transducer made by the Schmitt approach accordingly runs into the hundreds of dollars, at the present (1986) monetary scale.

This level of cost might conceivably be acceptable for permanent implants, but in short-term diagnostic equipment it is essentially out of the question. For sterility reasons, workers skilled in the art of short-term diagnostic cardiovascular catheters generally concur that such catheters must be discarded after just one use!

As to such disposable cardiovascular catheters, the costs of materials must be kept in the range of pennies and dollars. Only by such restraint can the overall price of a finished catheter with all component subsystems be, say, between one and two hundred dollars at most.

The general approach of Schmitt has been followed in an even more remotely related type of instrument reported in the paper "A New Noninvasive Backscattering Oximeter," by T. M. Donahoe and R. L. Longini, published in the *Proceedings of the Seventh Annual Conference of the IEEE/Engineering in Medicine and Biology Society*, in volume 1 of 2, at page 144 (1985).

Donahoe and Longini do not discuss cardiovascular catheters—or, indeed, catheters of any type, or for that matter any other device that is immersed in blood, or cardiovascular expeditions by any technique. Their invention is, however, an optical device for determining blood-oxygen saturation—and a parameter that is analogous to hematocrit as well.

The Donahoe system is a reflectance oximeter that is applied to external surfaces of the patient's body. It includes a light source that, in use, is positioned directly against the patient's body tissue, so that light from the source passes directly into the tissue.

The system receives light that is backscattered by the tissue itself and also by whatever blood is present within the tissue. The device receives the scattered light at two separated detectors, both also positioned directly against the patient's body tissue—so that light passes directly from the tissue into the detectors.

The detectors, however, are at fixed, known distances from the source; and the differential in source/detector distance is used to measure so-called "tissue hematocrit": volume of blood corpuscles per unit volume of body tissue.

It would be very desirable to provide at practical levels of cost a short-term diagnostic cardiovascular catheter system, capable of both hematocrit-corrected oxygen-saturation measurements and independent hematocrit measurements within the immediate cardiac system.

The 1984 Schmitt system provides such measurements, but at prohibitive cost. The 1985 Donahoe system provides only analogous measurements, for the periphery of the body.

A much more recent paper of J. M. Schmitt, F. G. Mihm and J. D. Meindl, appearing in *Annals of Biomedical Engineering*, volume 14, page 35 (1986) describes a transducer system for mounting at the end of a cardiovascular catheter. We mention this paper here for completeness, although it does not appear to be prior art with respect to the present document.

This later Schmitt et al. transducer, except for its positioning on a cardiovascular catheter, is similar to that described by the related group of authors in 1984.

The comments made above regarding prohibitive cost levels of the earlier system are equally applicable to the more recent one. Even the newer Schmitt system, although interesting, fails to satisfy modern diagnostic needs for small, highly precise instrumentation.

In particular, the Schmitt group reports measurement variation of "about 19%" (root-mean-square deviation). That value is an order of magnitude too large for state-of-the-art medical practice.

Furthermore, Schmitt's optical-sensor package was six millimeters long, two millimeters wide and one millimeter thick. Although the authors believed it "possible" to reduce the width to about one millimeter, even with such a reduction the package would be much too large to fit on the tip of a cardiovascular catheter for use in human beings.

SUMMARY OF THE DISCLOSURE

Our invention is a system for determining the corpuscular content of a fluid that contains a varying quantity of corpuscles. It includes some means for emitting light, and some means for detecting light.

For purposes of speaking generally, we will refer to these means as the "light-emitting means" and "light-detecting means." (We will employ analogous terminology to other parts of our invention which are deserving of broad, general characterization.)

Both the light-emitting and the light-detecting means are remote from the fluid of interest. As an example, the fluid may be blood in a patient's pulmonary artery, and the emitting and detecting means may be in an equipment module that is just outside the patient's body. Our invention is amenable, however, to implementation over considerably longer distances in other applications.

Our invention also requires some means for transmitting light from the remote light-emitting means by way of the fluid under test to the remote light-detecting means. It is quite important to our invention that this light transmission occurs along two paths—usually parallel paths. In accordance with our invention, these means for transmitting light must include one or more optical fibers; hence we shall call these means the "optical-fiber means."

Each of the two paths provided by the optical-fiber means includes two segments. There is a first optical-fiber-means segment for directing light from the remote emitting means to the fluid. This first segment terminates in light-projecting means disposed adjacent to the fluid.

In each of the two paths there is a second optical-fiber-means segment for directing light from the fluid to the remote detecting means. This second segment commences in light-receiving means that are disposed adjacent to the fluid.

These light-receiving means receive light after scattering by the fluid and by any corpuscles that are within that fluid. In other words, the light in proceeding from the first to the second segment passes at least shallowly through the fluid.

The first segment and its light-projecting means for one of the two paths have a first fixed, known geometrical relationship to the second segment and its light-receiving means for that one path.

Similarly, the first segment and its light-projecting means for the other of the two paths have a second fixed, known geometrical relationship to the second segment and its light-receiving means for that other path. It is particularly important that the second geometrical relationship be different from the first.

It is by virtue of this difference between the geometrical relationships between first and second segments for the two paths that the intervening segments—that is, the light trajectories that are formed within the fluid, between the first and second segments, and that include scattering within the fluid—are made different for the two paths. This difference between the intervening segments, in turn, offers a means of measuring corpuscular concentrations of the fluid.

Finally, our invention includes some means for comparing the light respectively transmitted along the two paths to determine the quantity of corpuscles. These means, which we will call the "interpretation means," are responsive to the light-detecting means; and in their operation they take into consideration the two known, different geometrical relationships.

The system just described may be a general implementation of our invention considered in its broadest terms. It includes several variant forms. In particular, all four optical-fiber-means path segments may be distinct, discrete subpaths; or one of the optical-fiber-means segments may be used by both paths in common.

In the latter case, there are only three distinct, discrete optical-fiber-means subpaths. Such a form of our invention can in turn occur in two variants.

In one such variant, there may be just one source, and one optical-fiber-means segment may be employed to direct light from the one source to the fluid—but the return paths, the "second optical-fiber-means segments" of the two paths, are distinct from one another. That is, there are two discrete detectors and each of the two distinct "second segments" directs light from the fluid to a respective one of the two detectors.

The other variant is the reverse—two sources, and two "first segments" directing light into the fluid; and a single "second segment" with corresponding detector used in common for the return.

Another set of possibilities (for either of these two variants) is that the distinct optical-fiber-means segments use a common source or detector, but the effects of propagation along different paths are separated from one another in time or in frequency by—for example—alternate chopping or other modulation schemes. By such timing distinctions or the like, the common source or detector in effect serves as two distinct sources or detectors.

There is still another set of possibilities, cutting across all of the variants already discussed. The three or four physically discrete optical-fiber-means path segments may be separated from one another by being in discrete fibers; or it is also possible that two or more may share a single fiber.

As to the latter case, it possible that adequate physical separation may be obtained by use of different modes of propagation within the fiber. Such modal separation may also provide adequate physical separation outside the fiber, for the previously mentioned intermediate path segments—that is, those within the fluid.

Any of these several forms of our invention may be greatly enhanced by provision of additional elements enabling the system to measure also the chemical content of the fluid. For example, when the basic invention as already described is used to determine hematocrit in blood, spectral effects can be used to determine oxygen saturation of the blood, using either one of the two paths from source to detector.

All of the foregoing operational principles and advantages of the present invention will be more fully appreciated upon consideration of the following detailed description, with reference to the appended drawings, of which:

BRIEF DESCRIPTION OF THE DRAWINGS

FIG. 1 is a somewhat schematic view, which may be considered either a plan or an elevation, of a catheter in accordance with a preferred embodiment of our invention. Because of the considerable length of the instrument, it is drawn partially broken away.

FIG. 2 is a greatly enlarged cross-section of the same embodiment, taken along the line 2—2 in FIG. 1.

FIG. 3 is an enlarged elevation or plan of the same embodiment, showing the balloon in longitudinal section, near the distal end of the catheter.

FIG. 4 is a greatly enlarged end elevation of the same embodiment, taken along the line 4—4 in FIGS. 1 and 3 at the distal end of the catheter.

FIG. 5 is a similarly enlarged longitudinal-section bottom plan view of the same embodiment, taken along the line 5—5 in FIG. 4.

FIG. 5a is a similarly enlarged longitudinal-section elevation of the same embodiment, taken along the line 5a—5a in FIG. 4. The two longitudinal sections 5 and 5a are taken at right angles to one another.

FIG. 6 is an enlarged elevation or plan of the same embodiment, partially in longitudinal section, at the proximal end of the catheter—and including an optical connector that terminates the optical-fiber means of our invention.

DETAILED DESCRIPTION OF THE PREFERRED EMBODIMENTS

Figure 7:
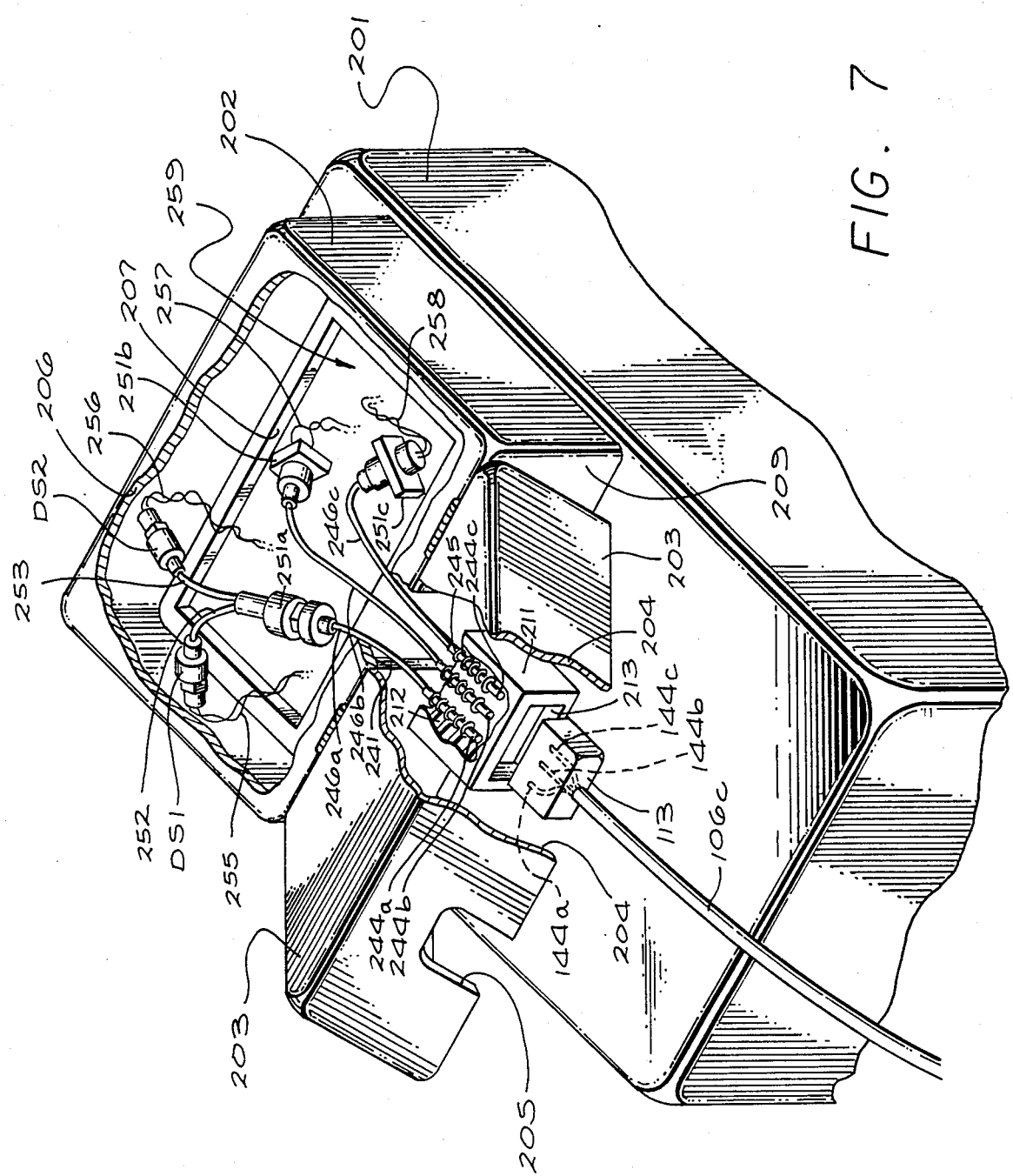
FIG. 7 is a generally isometric or perspective and somewhat schematic drawing of the mechanical portions of an optics module for use with the FIG. 1 catheter—and adapted to connect with the optical connector shown in FIG. 6.

Our invention has broad utility. Its embodiments of greatest current interest to us, however, are all in the area of cardiovascular diagnostic systems.

As shown in FIGS. 1 and 2, the preferred embodiment of our invention makes use of a five-lumen catheter 101. It will be understood that ur present invention can instead be implemented in a catheter having more or fewer lumens, or even only one lumen, but we believe that the full potential of the invention is best realized in a multiple-function catheter generally as described below. The catheter diameter is preferably 7.5 French or less.

Fixed at the proximal end of the catheter 101 are a manifold connector 105 and five individual single-lumen tubes 106. These individual tubes respectively communicate at their distal ends with the five lumens T/F, P, B, D and P/M of the catheter 101—through the manifold connector 105—and at their proximal ends with five termination devices 107.

Fixed at the distal end of the catheter 101 are a molded tip 102 and an annular balloon 104. In the tip 102 is the polished distal end F' (FIG. 4) of a bundle of optical fibers F (FIG. 2), that is drawn through the lumen T/F in the catheter 101.

Also in the tip 102 is a port or aperture D' (FIG. 4). This distal aperture D' effectively constitutes the distal end of one of the lumens D (FIG. 2) in the catheter 101. The remaining space in the orifice of the tip is occupied with epoxy or like inert potting material 136.

As is well known in the cardiovascular field, a catheter of this sort is inserted through the patient's vena cava into the right atrium and ventricle, with the tip 103 and its distal aperture D' extending onward into the pulmonary artery. The tip 103 generally is held in that artery for pressure measurements and optical measurements.

The arrangement of the polished ends of the optic fibers at F' appears in FIGS. 4, 5 and particularly 5a. As there suggested, the optic fibers are mutually aligned side-by-side and parallel in a linear array.

In FIG. 5, to permit showing of a greatly enlarged view, the "bottom" of the catheter is drawn broken off at 504. Similarly in FIG. 5a the "bottom" of the formed tip 102 is drawn broken off at 531, while the "bottom" of the optic-fiber bundle F' is drawn broken off at the lines 532.

We prefer to use three optic fibers nn, oo and pp that function to transmit light and a fourth piece of fiber rr that serves only as a spacer. The longitudinal section of FIG. 5 is taken through the spacer rr shown in FIG. 5a. This configuration is preferred for reasons to be set forth.

More specifically, we prefer to use one fiber nn to transmit light from a single source to the fluid under test, and two other fibers oo and pp to transmit backscattered light from the fluid to two separate detectors. The ends of the two other fibers oo and pp are differentially spaced—by an optically inactive fiber piece rr—from the end of the first fiber nn.

It will be understood, however, that the same drawings (FIGS. 4, 5 and 5a) will serve to illustrate the converse system, discussed earlier, in which two fibers oo and pp—whose ends are spaced apart by an optically inactive fiber piece rr—transmit light from separate sources to the fluid, and a single fiber nn transmits backscattered light from the fluid to a single detector.

In both cases, through calculation and experimentation we have found it desirable to enhance the difference between the intervening optical-path segments through the fluid by spacing the two fibers oo and pp apart. A particularly satisfactory geometry and stable mechanical arrangement are obtained by using as a spacer the fourth piece of optic fiber rr, which is preferably of the same cross-section.

As will be apparent, in purest principle any number of different kinds of materials could be used for the spacer rr. Moreover, in principle the spacer rr could be of entirely different size and cross-sectional shape—e.g., square, rectangular, or in any of a great variety of elaborate forms.

Using a short piece of the same fiber stock as used for the light-transmitting fibers nn, oo, pp is particularly desirable, however, since all four fibers can then be expected to respond identically to temperature changes and other forms of stress and shock. Such identical response renders the assembly particularly stable and strong.

For further stability the space 533 below the spacer rr may be filled with a suitable adhesive material. If desired, the bottom end of the spacer rr may be tapered to minimize the amount of space to be so filled.

FIGS. 5 and 5a, and particularly FIG. 4, can also be taken as representing yet another above-discussed system in which two fibers nn and oo transmit light from separate sources, and two fibers pp and qq (not visible, implicitly out of the plane of the paper behind or in front of pp) return backscattered light from those separate sources to corresponding separate detectors. Light from the separate sources can be distinguished as by time multiplexing.

Now for definiteness our discussion will return to the system which we prefer—in which the two spaced-apart fibers oo and pp are the detector fibers, and the one other optically-active fiber nn is the source fiber.

We have observed that light from the source fiber nn backscattered into the detector fibers oo and pp is strongly dependent upon hematocrit (or, more generally, corpuscularity) in the test fluid. Such backscattering, however, at the oxygen-saturation isobestic point is by definition independent of oxygen saturation.

Our invention uses the hematocrit dependence to develop a hematocrit measurement signal. Such a signal, however, is subject to variations due to source fluctuations, variations in the transmissive quality of optic fibers and particularly the condition of their tips, and also in optical qualities of the blood itself.

The absolute microscopic condition of an optical-fiber tip, particularly in its optical interaction with the blood, is virtually impossible to assess except by actual transmission tests with the tip immersed in blood. Consequently it is extremely desirable to obtain a reference signal in which the tip condition and other essentially uncontrollable variables are at least largely cancelled by some ratioing process—thereby bringing the system within reasonable range of similarity of operating conditions to some practical precalibration procedure.

We have considered and rejected the idea of providing a reference photodetector not connected to the catheter. In the system described here, one detector fiber pp (and its associated detector) may be regarded as the primary signal path, while a reference signal is in effect obtained from the other detector fiber oo (and its detector).

Perhaps in abstract principle, either fiber could be regarded as the reference detector. Since, however, the optical signal in the fiber pp that is farther from the source fiber nn is more strongly dependent on hematocrit than the optical signal in the nearer fiber oo, we prefer the nomenclature established in the preceding paragraph.

It is important to note that the hematocrit measurement obtained with our invention requires light at only one wavelength—and, in particular, light at the isobestic wavelength that is generally used to compute oxygen saturation of blood. Hence, our invention can be used without any additional light source to obtain and read out an independent measurement of hematocrit—and then to correct oxygen-saturation measurements for the hematocrit level.

The independent hematocrit readout is of value to the practicing clinician. The prior art, however, only corrects oxygen saturation for hematocrit without independently determining and reading out the hematocrit value.

The balloon 104, as better seen in FIGS. 3 and 5, is formed as a short length of latex tubing, positioned over a necked-down end section 131 of the catheter 101. The distal end of the balloon tubing 104 is doubled under and is held by adhesive 501 to the neck portion 103 of the tip 102.

The proximal end of the balloon tubing 104 is held by adhesive 135 to the proximal end of the necked-down end section 131, and the tapered annular space just proximal to the balloon is filled with epoxy or like cement 503. A very small balloon-inflation aperture B' is defined in the necked-down end section 131 of the catheter 101, communicating with the dedicated balloon lumen B (FIG. 2).

Three or four centimeters proximal to the tip 102 an aperture T/F' (FIG. 1) is formed in the catheter wall, communicating with the lumen T/F (FIG. 2). This aperture is occupied principally by a thermistor bead T' (FIG. 3), functionally connected at the distal end of the thermistor leads T (FIG. 2). The remainder of the aperture T/F' is filled with urethane or like potting compound 137.

(In FIG. 3 as well as FIG. 1, the catheter 101 and its complementary individual tubes 106 are drawn broken away in their uniform, undistinguished portions 108, to permit illustration of the diameter at a practical scale.)

In use, the balloon 104 and thermistor T' are generally passed with the tip 103 into the patient's pulmonary artery. Temperature information developed with this part of our system thus relates to the blood in that artery. As is well known in the field, such information can be used to monitor passage through that artery of a cold bolus of liquid injected at a known point upstream—as, for example, in the right atrium.

By monitoring the blood temperature (often designated $T_b$) in that artery, the instrumentation can develop data on the pumping capacity or pump flow rate of the heart, usually called "cardiac output." Accuracy of these data is enhanced by comparing the measured blood temperature with the preinjection temperature of the injectate alone. The latter temperature (correspondingly designated $T_j$) is measured using a separate thermistor, not illustrated.

As indicated roughly in the drawing, the thermistor leads T share the lumen T/F with the optic fibers F. To minimize assembly cost the thermistor leads T and optic fibers F should be drawn together through the thermistor-and-fiber lumen T/F. Doing so may have another advantage—namely, minimizing the risk of damage to both the leads T and the fibers F.

Eighteen to twenty centimeters proximal to the tip 102, another aperture P/M' is formed in the wall of the catheter 101, this one in communication with the lumen P/M. This lumen P/M and aperture P/M' can be left unobstructed, for measurement of pressure in the right ventricle through a fluid column in the lumen; or when desired can be used for heart pacing, as described below.

Within the lumen P/M, extending outward from the catheter 101 through the aperture P/M' is a coaxial wire 139. In use, it is typically positioned in the patient's right ventricle, lying against the myocardium or heart muscle.

Near the tip of the portion of the wire that extends out through the aperture P/M', the central conductor of this wire 139 is exposed so that the outer and inner conductors form an electrode pair for application of pacing voltage pulses to the myocardium. Unused clearance space within the lumen P/M and its aperture P/M' can be used for drip administration of medication—including, for example, dilute heparin solution or other anticoagulant to help maintain the lumen P/M and its aperture P/M' (FIG. 1) free of blood clots.

Just distal from the pacing-and-medication aperture P/M', a very short length of stainless-steel spring wire (not shown) is inserted into the lumen P/M. This wire serves to plug the unused, distal portion of this lumen, and also to form a radiopaque marker that can be helpful in positioning the catheter with the aperture P/M' in the patient's right ventricle for proper pacing.

Twenty-eight to thirty centimeters proximal to the tip 102 of the catheter 101, another aperture P' is formed in the catheter wall, communicating with the lumen P. In use this proximal aperture P' is typically positioned within the patient's right atrium, and is used for injection of a cold bolus in the thermodilution method of cardiac output (flow rate) measurement. This same aperture P' can also be used to measure pressures.

Just distal from the proximal aperture P' a very short rod of solid polyvinyl chloride or the like is inserted into the corresponding lumen P, to block off the unused, distal portion of this lumen.

To aid in determining how much of the catheter's length has been inserted into the patient's body during the initial phases of the catheterization process, markers are advantageously imprinted along the outside of the catheter at suitable intervals. For example, indicium 121 may be placed at ten centimeters from the tip 102, indicium 122 at twenty centimeters, and indicium 123 at thirty centimeters.

Each of these indicia may be a simple narrow band or group of narrow bands, each band representing a cumulative ten centimeters. More than four bands being hard to count quickly, however, it is helpful to use a single broader band for the fifty-centimeter indicium, and then a broad band next to a narrow band to represent fifty-plus-ten or sixty centimeters, etc. Thus the one-hundred centimeter indicium 124 appears as a pair of broad bands.

Individual termination devices 107 at the proximal end of the catheter include a stopcock 111, communicating with the balloon lumen B, and a first hub or extension port 112 communicating with the distal-aperture lumen D. Thus the stopcock 111 is for inflating (or deflating) the balloon 104. The port 112 is used for measuring pulmonary-artery pressures or injecting medication into that artery—or, on a drip basis (as with anticoagulant heparin, at three to six milliliters per hour), both simultaneously.

The termination devices also include a fiber-optic connector 113, connected with the optic fibers F in the thermistor/fiber lumen T/F. The polished proximal ends 144 of the fibers F are presented at the proximal side of the connector cap 143 for connection to a mating device (not illustrated) that provides the necessary light sources, detection and interpretation.

In addition, the termination devices 107 include an electrical connector 114, which provides connection points for the thermistor leads T. A threaded section 146 is advantageously provided at the proximal side of the connector cap 145 to securely engage a mating connector of an electronics module that provides excitation and interpretation for the thermistor T'.

Also among the termination devices 107 are two other hubs 115 and 116. Of these, one port 115 communicates with the proximal lumen P, for injection of a cold bolus in thermodilution cardiac-capacity tests. The other port 116 connects with the pacing-and-medication lumen P/M to guide the coaxial pacing wire 139 (and drip medication) to the right ventricle. A Touy-Borst connector allows both electrical hookup to the wire and injection of medicine. (If preferred, the pacing wire 139 can be omitted, and instead a fluid column can be established in the lumen P/M for right-ventricle pressure measurement at the port 116.)

The stopcock 111 and the hub or extension ports 112, 115 and 116 all end in respective liquid-transfer fittings 141, 142, 147 and 148—which are adapted for pressurized attachment of hypodermic-style injecting apparatus.

Additional details of the termination device 113 for the optic fibers appear in FIG. 6. That drawing also presents added details of the termination device 114 for the thermistor leads. The other intermediate tubulations 106 are drawn broken off at 524.

As shown in the drawing, we prefer to configure the optic-fiber connector 113 as a formed housing 113a that has three integral sides and an integral distal end, and that also has a cover 113b along a fourth side. A stress-relief fitting 523 is provided to minimize the potential for damage to the optic fibers within the fiber bundle 106c.

The proximal end of the housing 113a is covered by a cap 113c in which are formed three precisely positioned ferrules 521a, 521b and 521c. Firmly secured within these ferrules are proximal optic-fiber tips 522a, 522b and 522c respectively.

The ferrules 521a, b, c and corresponding fiber tips 522a, b, c may be ground and polished together, to provide good mechanical and optical mating with detection and interpretation apparatus to be described below. By virtue of precision in their lateral positioning within the cap 113c, the ferrules assure adequate lateral alignment of the fiber tips with the detection apparatus.

Through the length of the catheter 101, and particularly through the lumen T/F previously discussed, these three proximal optic-fiber tips 522a, 522b and 522c are respectively continuous with the three distal optic-fiber ends nn, oo and pp of FIGS. 5 and 5a.

FIG. 7 illustrates generally the mechanical arrangements for optical linkage of the fiber tips 144a, b, c to the emitters and detectors. That drawing illustrates generally a small electronics cabinet 201, for placement beside a patient who is to be catheterized. The interior 259 of the cabinet 201 houses various signal-generating and -processing circuits to be described.

An auxiliary compartment 202 (drawn broken away at 206) is secured atop one end of the cabinet 201. The top panel of the cabinet 201 is apertured at 207 for free access as between the interior 259 of the cabinet and the interior of the auxiliary compartment 202.

A bulkhead 209 at one end of the auxiliary compartment 202 is apertured at 241 to provide limited access to the interior of the auxiliary compartment. An optical-connector receptacle 211 (drawn broken away at 212) is mounted in the aperture 241. A formed cover 203 (drawn broken away at 204), hinged to the same bulkhead, protects the receptacle 211 and the area just in front of that receptacle.

With the cover 203 raised, the connector 113 at the proximal end of the optic-fiber termination 106c is mated with the receptacle 211. The cover 203 is then lowered to protect the connection—while a notch 205 in the cover 203 permits passage of the optical termination 106c.

Inside the receptacle 211, three optical receiver segments 244a, 244b and 244c are disposed for alignment with the respective fiber tips 144a, 144b and 144c when the connector 113 is present. The receiver segments 244a, b and c have polished distal ends spring-loaded as at 245 toward engagement with the respective fiber tips.

Secured to the proximal ends of the receiver segments 244a, b and c for effective optical-signal transmission are respective optic fibers 246a, 246b and 246c. The optical signals pass outward from light emitters toward the catheter through one fiber 246a, and inward from the catheter toward the detectors through the other two fibers 246b and 246c.

Red and infrared signals in the "outbound" fiber 246a originate in light-emitting diodes DS1 and DS2, respectively excited through electrical-signal leads 255 and 256 from pulse-generating circuitry within the cabinet 201. These optical signals pass from the diodes DS1 and DS2 through respective optic fibers 252 and 253 to a "mixer" section 251a, which combines the signals and passes them on into the fiber 246a.

"Near" and "far" fiber optical signals returning through the other two fibers 246b and c proceed to respective combination detector-amplifier-buffer units 251b and 251c. These units provide electrical signals of intermediate impedance in respective leads 257 and 258 for passage to signal-processing circuitry that is also within the cabinet 201.

The light-emitting diodes DS1 and DS2, the mixer unit 251a, and the combination detector-amplifier-buffer units 251b and 251c are all drawn in combination with their respectively associated optical connectors. All or some of these units may be allowed to "float" (i.e., to be suspended by their attached optic fibers and electrical leads) as illustrated.

For best measurement reproducibility, however, we consider it advisable to provide better mechanical stability. We prefer to mount at least the diodes DS1 and DS2 and the combination detector-amplifier-buffers 251b and 251c to circuit boards disposed within the cabinet 201.

Figure 8:
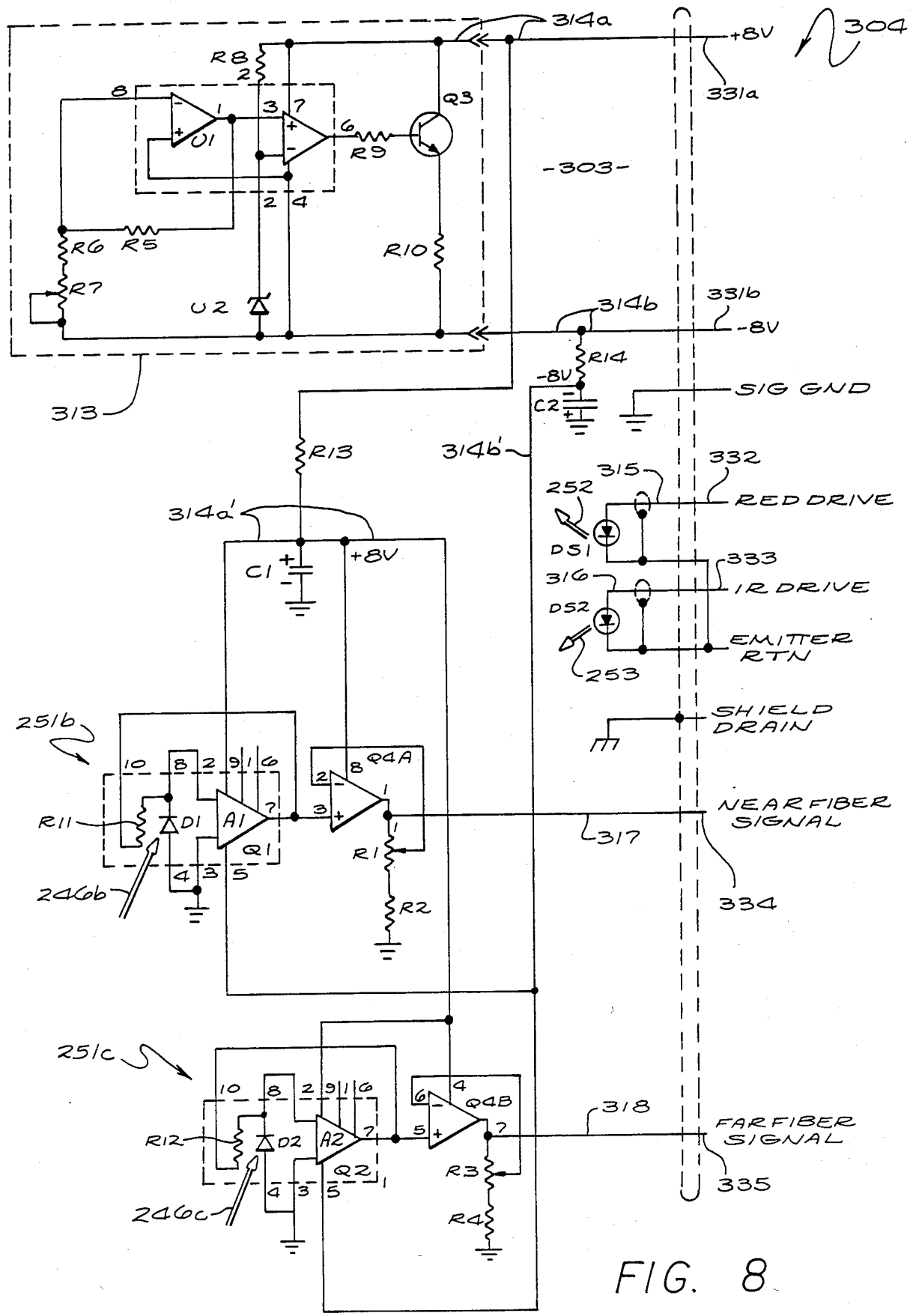
FIG. 8 is an electrical schematic drawing of the various electronic parts of the FIG. 7 optics module.

FIG. 8 represents the active portions of an electrical module to be housed within the cabinet 201. (The cabinet optionally may also provide through-connections to the thermistor wires, not shown in FIG. 8—or if preferred the temperature-signal cabling may be provided separately.)

This module 303 receives regulated positive and negative supply voltage through respective leads 331a and 331b of a shielded cable, for distribution by respective leads 314a and 314b within the patient-side module to a thermal-control unit 313 and to respective ripple filters R13-C1 and R14-C2. From these filters the supply voltages pass to the integrated detector-amplifier units 251b and 251c.

Passing through the cable 304 in addition to the supply voltages are emitter-excitation signals, in two leads 332 and 333. Within the patient-side module 303 these signals proceed directly via respective leads 315 and 316 to the light-emitting diodes DS1 and DS2. These diodes respectively project the red and infrared signals into optic fibers 252 and 253. These both lead to a common optical mixer 250.

The thermal-control unit 313 is included to stabilize the temperature of the light-emitting diodes DS1 and DS2. It accordingly stabilizes the intensity and spectral distribution of their emission, which can be significant in achieving adequate photometric accuracy for hematocrit determination—and very important in achieving adequate spectrometric accuracy for oxygen determination.

Within the thermal-control unit 313, an operational amplifier U1 compares a reference voltage (produced at a temperature-sensitive reference diode U2) with a voltage developed by the resistive divider R5-R6-R7. The divider includes the first-stage feedback resistor R5, which directly affects the first-stage gain, and bias resistance consisting of R6 and a sensitive trimming resistor R7.

The amplifier U1 produces a difference signal which controls the current level in a power transistor Q3. This transistor (as well as its load resistor R10) serves as a heater, controlling the temperature of the temperature reference diode U2 and thereby shifting the operating point of the amplifier U1.

The sense of the shift is such as to oppose changes in the temperature of the resistor string R5-R6-R7. In the process the heater also controls and stabilizes the temperature of the diodes DS1 and DS2.

As mentioned above, ripple-filtered power is applied to integrated detector-amplifiers 251b and 251c. Each of these units includes an integrated-circuit detector-amplifier Q1 or Q2, each with its own respective light-sensitive diode D1 or D2, a corresponding load resistor R11 or R12, and an amplifier A1 or A2.

Optical signals in the associated optic fiber 246b or 246c cause conduction in the diode, drawing down slightly the input voltage to the amplifier A1 or A2. An amplified version of the diode voltage accordingly appears at the output terminal of the integrated-circuit detector-amplifier Q1 or Q2.

This amplified Q1 or Q2 output is applied to one stage Q4A or Q4B of an operational amplifier, which is also part of the combination detector-amplifier 251b or 251c. Each operational-amplifier stage Q4A or Q4B is wired in its respective circuit as a cathode follower.

Each combination detector-amplifier-buffer 251b or 251c thus provides an amplified and buffered "near fiber" or "far fiber" electrical signal on its output lead 317 or 318, for conduction to the main electronics unit by a corresponding conductor 334 or 335 in the cable 304.

Figure 9A:
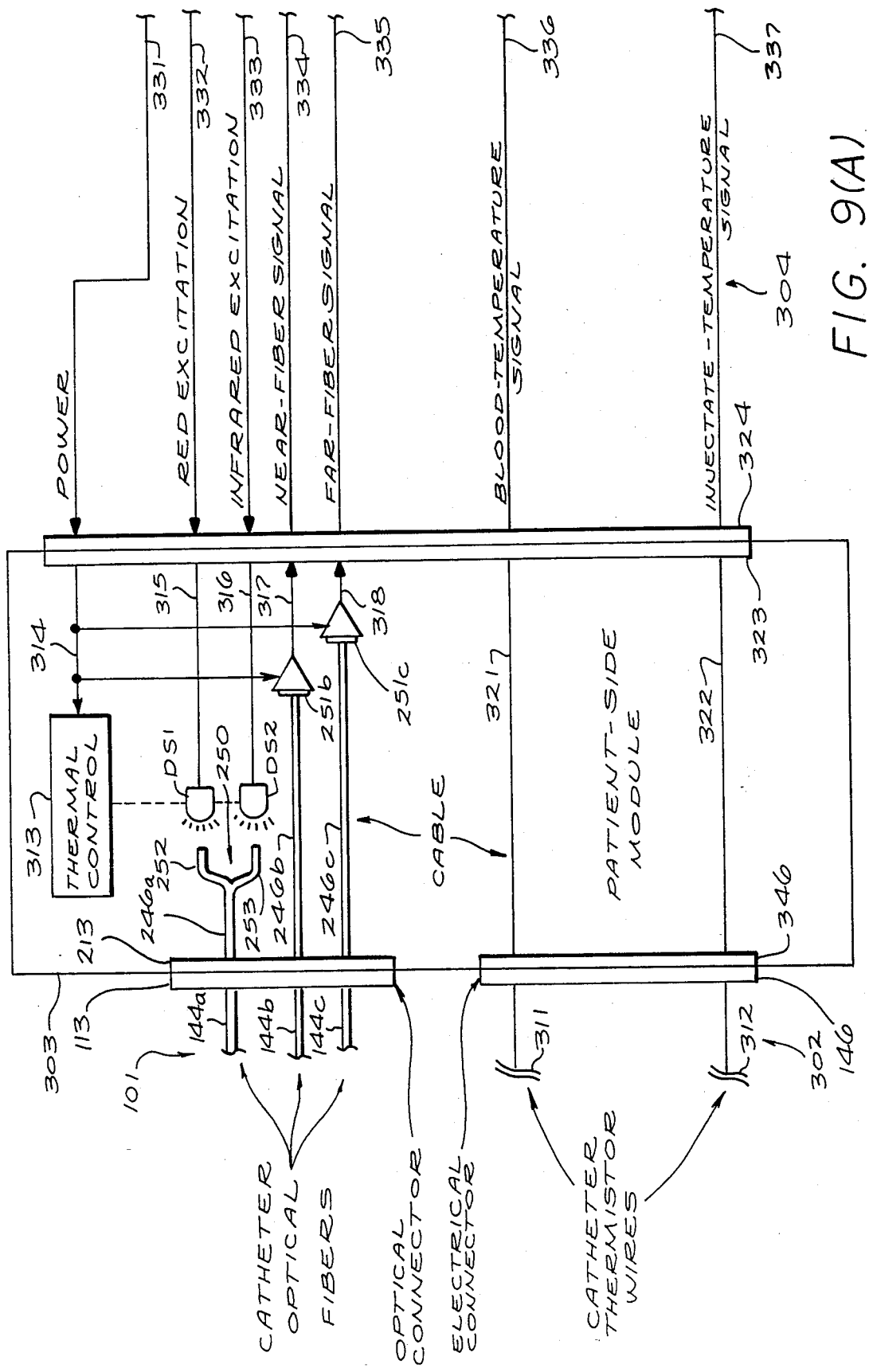
FIGS. 9A, 9B, 9C are a schematrc drawing of an entire catheter system according to our invention, particularly including the catheter of FIGS. 1 through 6, the optics module of FIGS. 7 and 8, and electronics that interact with the catheter through the optics module to produce a display, printout and voltage outputs representative of the data obtained by the system.
Figure 9B:
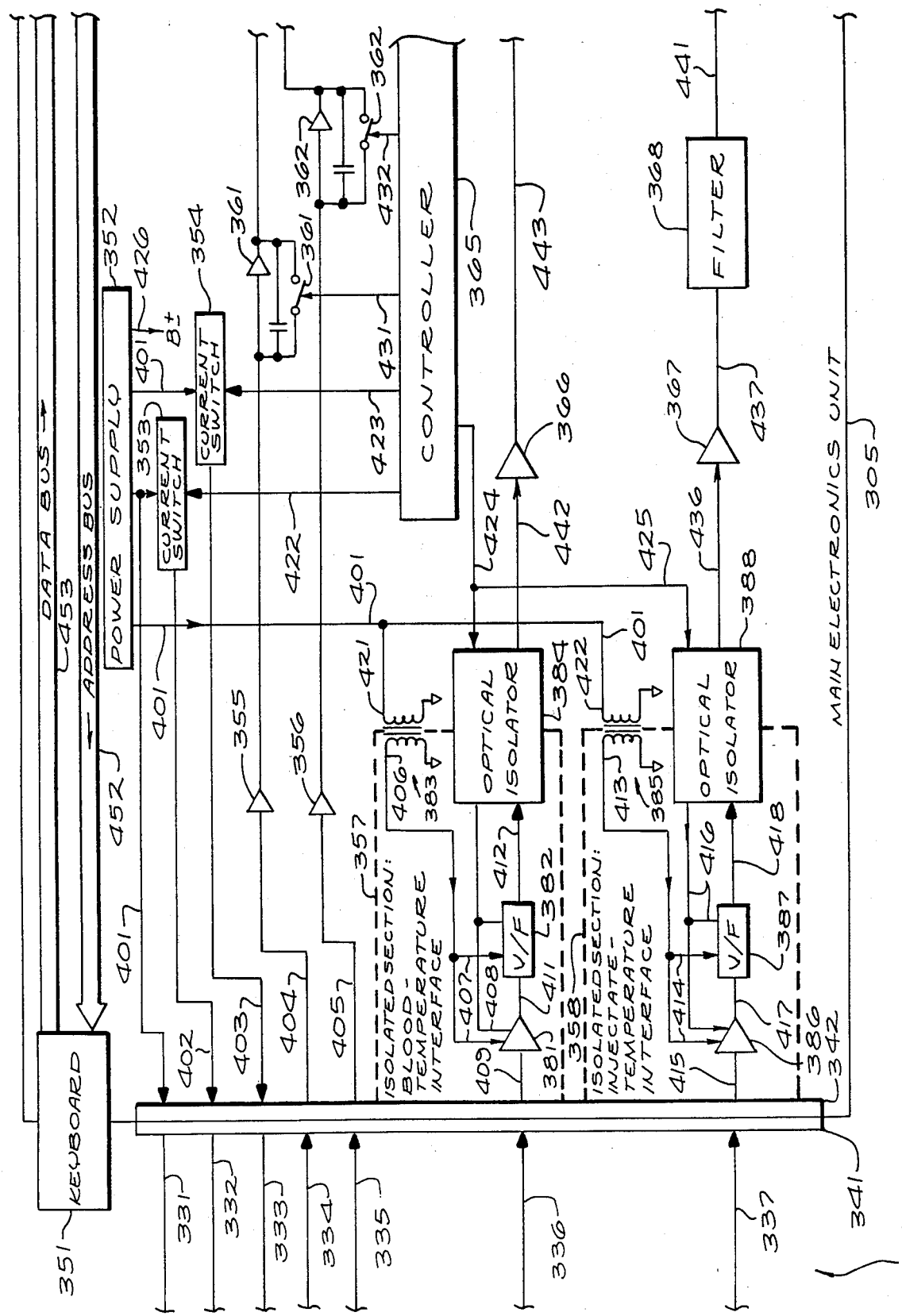
Figure 9C:
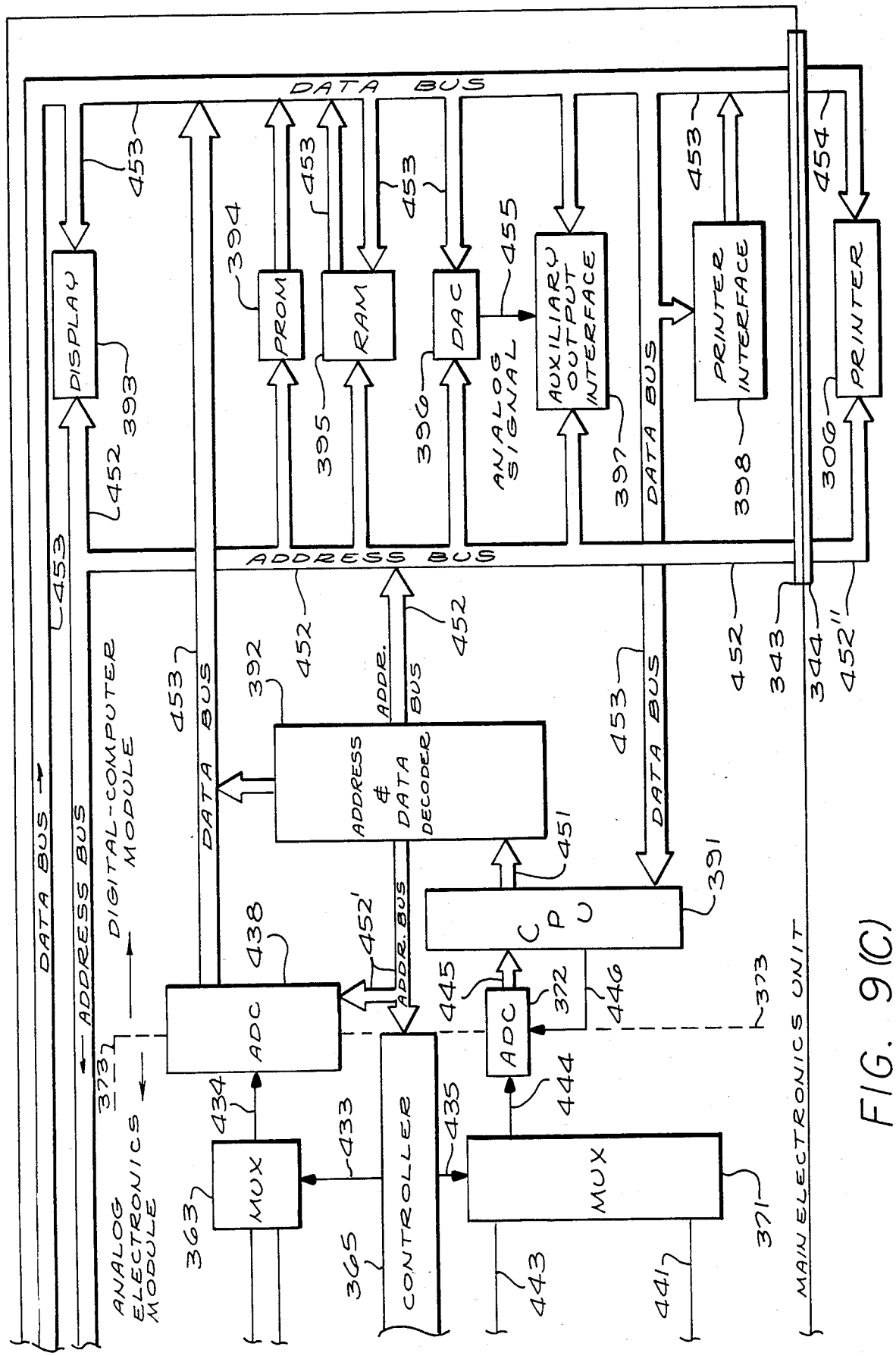

The functions of the patient-side module 303 also appear more schematically in FIG. 9 in conjunction with the remainder of the circuitry, which is primarily in the main electronics unit 305. Other modules such as a printer 306 may be incorporated into the system as appropriate.

FIG. 9 also shows the optical connector 113-213, and the catheter optical terminations 144a, b and c, which were previously discussed in connection with FIG. 7. Further, FIG. 9 illustrates that the patient-side module 303 may include through-connections 321 and 322 for the thermistor signals; alternatively, we may prefer to provide separate temperature-signal cabling directly from the main electronics unit 305, for one or both of the thermistors.

These through-connections 321 and 322 are wired at one end to an electrical connector 146-346 for the catheter electrical terminations 302. As seen in FIG. 9, the through-connections 321 and 322 are wired at their other end to the previously mentioned connector 323-324, which serves the cable 304 to the main electronics unit 305.

Most of FIG. 9 is devoted to showing the main electronics unit 305. That unit generates the necessary electrical excitation for production of the optical probe signals—and interprets the electrical signals returned as a result of the interaction of those probe signals with the blood (or other fluid under test).

A power supply 352 within the main electronics unit 305 develops positive and negative supply voltages as at 426. These voltages are for distribution to generally all the power-consuming modules within the main electronics unit 305 proper.

The power supply 352 also provides positive and negative voltages at leads 401 for certain uses that are individually illustrated. These uses include supply of the patient-side module 303, as previously mentioned, via certain leads 331 of its cable 304.

The individually illustrated use points also include two current switches 353 and 354, and the primaries 421 and 422 of two power-isolation transformers 383 and 385 respectively. The current switches 353 and 354 are actuated by control signals at 422 and 423 from an electrical controller 365.

Under direction of the controller 365, the switches 353, 354 "chop" or time-modulate the excitation signals 402-332-315 and 403-333-316 to the red and infrared light-emitting diodes DS1 and DS2 respectively. The switches 353, 354 conduct in alternation, separated by time intervals in which neither switch makes contact.

Hence the diodes DS1 and DS2 emit alternately, separated by "dark" intervals. This modulation pattern, thus imposed upon the discrete optical signals through the optic fibers 252 and 253 to the optical mixer 250, of course persists in the composite optical signal through the outbound fibers 246a in the patient-side module 303 and 144a in the catheter 101.

It appears also in both of the two composite optical and electrical signals returned via the two return fibers 144b and 144c in the catheter 101, and 246b and 246c in the patient-side module 303. In other words, the red and infrared signals are multiplexed on both signal paths—and not only on the two return fibers, but also on their associated detectors 251b and 251c, and the associated electrical-signal lines 317 and 318.

In this way the modulation enables the signal-interpreting part of the circuitry to sort out the red-absorption data from the infrared-absorption data, and both from the background noise occurring during the "dark" intervals, in the returned signals. That part of the circuit will be discussed shortly.

While the controller 365 directs the operation of the current switches 353 and 354, the controller in turn receives "address" information (via part of an address bus 452') from a microprocessor or "central-processing unit" (CPU) 391, through an address-and-data bus 451 and an address-and-data decoder 392.

With respect to the light-emitting diode excitation signals 402-332-315 and 403-333-316, the controller 365 is thus in effect an interface between the analog and digital modules or sections of the main electronics unit 305. Analogous specific functions of the controller 365 will be noted below.

The supply of power at 401 through isolating transformers 383 and 385 is part of a guarding system. This system permits the blood-temperature interface 357 and injectate-temperature module 358 to be electrically isolated or "floating" relative to all the voltages in the entire system.

Such isolation is important: the two temperature interface modules are electrically connected to thermistors which in use are disposed within a patient's body, and more particularly within the patient's heart.

Such connections pose extreme hazard of severe and even fatal electrical shock, unless the wires are well-guarded against accidental engagement with even low-voltage circuit elements. Accidental contacts can otherwise result from, e.g., circuit-element failure, power-line transients, or improper electrical maintenance.

The blood-temperature and injectate-temperature interfaces receive signals from, respectively, a thermistor in the catheter and a thermistor that is in thermal contact with the injectate. As previously outlined, these signals are used in determining cardiac output by the thermal-dilution method.

The interfaces 357 and 358 receive the thermistor signals via catheter electrical terminations 302 (drawn broken away at 311, 312 in FIG. 9); and via leads 321, 322 in the patient-side module and leads 336, 336 in the cable 304.

The thermistor signals then enter the isolated interface sections 357 and 358 along leads 409 and 415, passing to respective buffers 381, 386 and thence by signal leads 411, 417 to V/F units 382, 387. These units are powered from the secondaries 406, 413 of the respective isolation transformers 383, 385.

Operation of the buffers 381, 386 and V/F units 382, 387 requires control signals for coordinated operation with the signal-interpretation circuits. Such control signals 424, 425 are supplied by the controller 365, again under direction of the CPU 391 and the address-and-data decoder 392.

To maintain the necessary electrical isolation, however, the control signals before entering the isolated interface sections 357, 358 are converted to optical signals by electrically energized light sources. Within the isolated sections these optical signals are then reconverted to electrical signals by photodetectors.

These conversions take place in the respective "optical isolators" 384, 388. The resulting photodetector outputs are applied at 408, 416 to the switching buffers 381, 386 and also to the voltage-to-frequency ("V/F") converters 382, 387.

Another source-and-detector pair connected for signal flow in the opposite direction carries the V/F outputs 412, 418 with electrical isolation into the main electronics unit proper. There they are transmitted at 442, 436 to respective amplifiers 366, 367.

The amplified signals 443, 437—with an additional filtering 368 of the injectate signal, to band-limit the signal and thereby prevent "aliasing" during later sampling for analog-to-digital conversion—are then applied at 443, 441 to a multiplexer 371. The multiplexer is synchronized by a signal 435 from the controller, which as for the earlier-mentioned functions is directed by the CPU 391 through the decoder 392.

The multiplexer 371 produces a single analog output signal 444 that is in effect a composite of the two temperature signals. This composite signal 444 proceeds to an analog-to-digital converter ("ADC") 372, which under direct control 446 of the CPU 391 generates a corresponding digital stream. The ADC digital output passes by an input bus 445 to the CPU 391.

Meanwhile the modulated excitation signals 402, 403 produce modulated red and infrared optical signals in the outbound optic-fiber termination 144a. (Depending on the spectral character of the phenomena to be analyzed in the fluid under test, some other two-wavelength pair of signals may be substituted.)

These signals traverse the catheter 101, and at the distal tip nn (FIG. 5a) of the same fiber enter the patient's blood or some other test fluid. The blood or other fluid scatters the red and infrared optical signals differentially—to a degree that depends on the degree of oxygenation, in the case of blood, or more generally on some spectrally sensitive phenomenon in the test fluid.

The differential scattering produces, in effect, differential attenuation of the red and infrared optical signals by the test fluid. Some of the differentially attenuated light within the fluid reaches and enters the distal tips pp, oo (FIG. 5a) of the return fibers.

These differentially attenuated red and infrared optical signals traverse both of the return fibers in the catheter to its proximal end. These signals are present in each of the corresponding catheter terminations 144b and 144c (FIGS. 7 and 9), and in each of the connections 246b and 246c within the patient-side module 303.

The optical signals reach the detector-amplifiers 251b and 251c and produce corresponding electrical signals 317 and 318. Still the spectral effects in the optical signals are separable in each of the electrical signals by virtue of the modulation previously imposed on the excitation signals.

In addition to the differential spectral effects just summarized, however, the optical signals also contain differential geometric information. As will be recalled, the latter is used to assess the blood hematocrit—or, more generally, analogous corpuscular phenomena within any test fluid.

Hematocrit or analogous particulate properties interact with the differential spatial separation (at the distal end of the catheter) of the receiving-fiber tips pp and oo from the emitting tip nn. The interaction permits calculation of hematocrit or the like from a comparison of the optical signals returned from the distal tips.

To implement this strategy, the electrical signals 317 and 318 from the patient-side module are kept separate. Respectively, they are identified as a "near-fiber signal" 317 (arising as an optical signal in the distal tip oo, and in the proximal termination 144b) and a "far-fiber signal" 318 (arising in the distal tip pp and the proximal termination 144c).

These electrical signals pass through respective leads 334 and 335 in the cable, and into corresponding leads 404 and 405 in the main electronics unit. Here the electrical signals, containing both spectral and geometric differential data, proceed to respective amplifiers 355 and 356.

The amplified signals are applied to respective "sample and hold" circuits 361 and 362, which are actuated by control signals 431 and 432 from the controller 365. A multiplexer 363, which is also actuated by a control signal 433 from the controller 365, forms a composite 434 of the amplified signals held in the sample-and-hold circuits 361 and 362.

All the spectral and geometric information is now present in the single composite signal 434. The various pieces of data in this signal are separable only by reference to the time multiplexing introduced at the current switches 353, 354 and the sample-and-hold circuits 361, 362.

The controller 365 is directed by the CPU 391, through the address-and-data decoder 392 as before, to generate the control signals 431, 432, 433. Since the single output signal 434 from the multiplexer 363 contains all the spectral and geometric data, the CPU must time the control signals to preserve all the spectral and geometric data in the electrical signals 404, 405.

The composite signal 434 from the multiplexer enters an analog-to-digital converter ("ADC") 438, which projects a corresponding digital signal into the data bus 453. This digital signal is directed via the data bus 453 to the CPU 391.

The digital signal from the ADC 438 is also available on the data bus 453 to various other elements of the system. These elements include the display 393, random-access memory ("RAM") 395, digital-to-analog converter ("DAC") 396, and printer interface 398.

The RAM 395 provides temporary storage of any information on the data bus 453. It also reads such data back into the bus on command, for later use.

The DAC 396 provides an analog equivalent 455 of any signal on the data bus 453 for passage to an auxiliary-output interface 397. This interface may be a serial output port for a telemetry connection, or any other appropriate external use.

The output signal from the printer interface 398 is naturally directed through a connector 343, 344 to an external-printer data bus 454. It is there used for generation of a permanent record by an external printer 306.

Thus in principle the ADC 438 output can be displayed, stored, telemetered or printed.

For most purposes, however, the digital signal from the ADC 438 is not suitable for direct display, storage, printout or other use. Like the multiplexer 434 signal, the ADC 438 output is a composite of both spectral and geometric information—that is to say, of both oxygenation and hematocrit information, in the case of blood.

Hence the ADC digital output generally is unintelligible in its "raw" form, and requires further processing in the form of calculations within the CPU 391. It is the results of these calculations are displayed, printed, or stored.

Several components have already been mentioned as destinations (or sources, or both) of the digital bus 453. The system also includes a keyboard 351, a programmable read-only memory ("PROM") 394, the address-and-data decoder 392, and an address bus 452.

An operator uses the keyboard 351 to enter various instrument settings, sample identifications, data-handling directions, and so on. From the keyboard 351 these various kinds of information generally proceed along the data bus 453 to the CPU 391 and in some cases also directly to the display 393 or the RAM 395.

Permanently stored in the PROM 394 are programs for sequencing of the controller 365 and of the various digital modules 351, 391–398. These programs include, in particular, instructions for internal operation of the CPU 391 to perform the necessary data separation and calculations.

The decoder 392 and the address bus 452 function in conventional fashion for digital control and computation devices. The decoder translates addresses and data as specified by the CPU 391 into a form usable by the other system elements 351, 393–398 and 306.

The address bus 452 carries the decoded addresses from the decoder 392 to the other system elements. In effect it parallels the data bus 453, identifying the particular memory, display, or other location where each data bit is to be "written" or "read."

The foregoing discussions will be sufficient to enable electrical design engineers and instrument programmers to prepare hardware and software for practice of our invention, except for the specific algorithms used in "massaging" the data from the thermistor-channel ADC 372 and from the optic-fiber-channel ADC 438. The thermistor data processing to derive cardiac flow rate or output is essentially conventional, and will not be discussed here.

As to the optic-fiber data, the PROM 394 should provide the CPU 391 with instructions to form the ratios:

$$x = IR_{near}/R_{near}$$

and $$r = IR_{near}/IR_{far},$$

where
- $IR_{near}$ is the infrared signal in the "near fiber,"
- $IR_{far}$ is the infrared signal in the "far fiber," and
- $R_{near}$ is the red signal in the "near fiber."

It will be noted that the system need not make any use of the red signal in the "far fiber."

The program then uses the ratios x and r to calculate both hematocrit Hct and oxygen saturation, in the case of blood—or analogous corpuscular and chemical characteristics in the case of other test fluids. The calculation proceeds by solving the following two equations:

$$Hct = Hr^3 + Ir^2 + Jr + K + Lx$$

and $$\text{oxygen saturation} = A(x-D)^2 + B(x-D) + C,$$

where:
- $B = E(Hct)^2 + F(Hct) + G$, and
- A, B, . . . J, K and L are constants characteristic of human blood.

In some prior-art cardiovascular work it is customary to use, for one of the optical signals, a so-called "isobestic" wavelength. That is a wavelength at which there is no difference between the scattering by oxygenated blood and the scattering by nonoxygenated blood.

Using an ideal isobestic wavelength, one should in principle be able to calculate the hematocrit from only the "near fiber" and "far fiber" signals. In practice, however, the wavelength available from infrared light-emitting diodes is not truly isobestic, and we accordingly prefer to correct for this slight dependence by including the term Lx in the above equation for hematocrit.

In applications involving vessels (whether test tubes or blood vessels) whose walls may be disposed near the catheter distal tip during use of the system, for best reliability the algorithms should include criteria and procedures for rejecting or correcting data that may be flawed by wall effects.

As is well known in this field, all components and materials that are to be exposed to the patient's cardiovascular system must be appropriately inert, amenable to sterilization, and preferably supplied sterilized.

Throughout the catheter portion of our invention, we prefer to use conventional sealant, potting, cementing and securing compounds generally available on the open market and familiar to cardiovascular-catheter artisans. Such materials are used, in particular, where the various parts (e.g., the manifold 105, catheter 101, and single-lumen tubes 106) are held together.

As to the electronics, referring to the system as illustrated in FIGS. 8 and 9, we prefer to use components having these circuit-element values or commercial part-designator numbers:

| | | | |
|---|---|---|---|
| U1 | LM10CN | R5 | 10 k |
| U2 | LM335AZ | R6 | 649 ohm |
| Q1 | S1406-04 | R7 | 200 ohm |
| Q2 | S1406-04 | R8 | 5.1 k |
| Q3 | MJE520 | R9 | 20 k |
| Q4A-B | TL082 | R10 | 30 ohm |
| DS1 | H2000K | R11 | 1000 M |
| DS2 | MFOE3201 | R12 | 1000 M |
| R1 | 10 k | R13 | 200 ohm |
| R2 | 200 ohm | R14 | 200 ohm |
| R3 | 10 k | C1 | 33 microfarad |
| R4 | 200 ohm | C2 | 33 microfarad. |

The positive and negative voltage supplies 401 for the patient-side module and to the current switches are advantageously ±8 volts. The supplies 426 are preferably ±8 and +5 volts.

The supply 401 to the isolation transformers 383 and 385 preferably includes a four-ampere-hour battery backup, and should be capable of supplying 800 mA through a chopper to the primary windings 421 and 422.

Within the isolated sections, if desired the supply voltage may be boosted slightly (by the isolation transformers) to ±9 volts.

The CPU 391 is preferably an eight-bit C-MOS type available commercially from NSC under the model number 800-1 The PROM 394 is preferably a 256 k unit, the RAM 395 preferably a 32 k unit, and the optical-channel ADC 438 is preferably a twelve-bit high-speed unit available under the designator ADC 1205. The DAC 396 may be an eight-bit unit.

The auxiliary-output interface is one of the type commercially identified as RS 232, and the display 393 is advantageously a four-line, fourteen-character liquid-crystal device. The keyboard 351 should have twenty keys, and the printer 306 may be a thirteen-column, five-by-seven-dot matrix type.

The red light-emitting diode should provide light at 660 millimicrons, and the infrared diode at 805 millimicrons. The patient-side-module cable is advantageously about three meters (ten feet) long.

It will be understood that the foregoing disclosure is intended to be merely exemplary, and not to limit the scope of the invention—which is to be determined by reference to the appended claims.

We claim:

1. A system for determining the corpuscular content of a fluid that contains a varying quantity of corpuscles, comprising:
   means, remote from such fluid, for emitting light;
   means, remote from such fluid, for detecting light;
   optical-fiber means for transmitting light from the remote light-emitting means via such fluid to the remote light-detecting means along two paths, each of said two paths including two segments:
      a first optical-fiber-means segment for directing light from the remote emitting means to such fluid, terminating in light-projecting means disposed adjacent to such fluid,
      a second optical-fiber-means segment, commencing in light-receiving means disposed adjacent to such fluid, for directing light from such fluid to the remote detecting means after scattering by such fluid and by such corpuscles therein;
   the first segment and its light-projecting means for one of the two paths having a first fixed, known geometrical relationship to the second segment and its light-receiving means for that one path;
   the first segment and its light-projecting means for the other of the two paths having a second fixed, known geometrical relationship to the second segment and its light-receiving means for that other path; said second geometrical relationship being different from said first geometrical relationship; and
   interpretation means, responsive to the light-detecting means, for comparing the light respectively transmitted along the two paths, to determine such quantity of corpuscles, taking into consideration said known geometrical relationships.

2. The system of claim 1, wherein:
   one of the optical-fiber-means path segments is used by both paths in common;
   whereby either the detecting means or the emitting means, but not both, is used by both paths in common.

3. The system of claim 2, also for use in measuring the chemical content of such fluid:
   wherein said light-emitting means emit light in a first particular wavelength band; and
   further comprising second light-emitting means that emit light in a second particular wavelength band;
   said first optical-fiber-means path segment also directing light in the second particular wavelength band from said second light-emitting means to such fluid;
   said second optical-fiber-means path segment also directing light in the second particular wavelength band from such fluid to the receiving means; and
   said interpretation means also comparing light in the two wavelength bands received by the light-detecting means, to determine the chemical constituency of the fluid taking into account said determined quantity of corpuscles.

4. The system of claim 1, wherein:
   the light-emitting means include one light source used by both paths in common;
   the light-detecting means include at least two different light detectors;
   one first optical-fiber-means segment is used by both paths in common to direct light from the one source to such fluid; and
   the second optical-fiber-means segments of the two paths are distinct from one another, each directing light from such fluid to a respective different one of the detectors.

5. The system of claim 4, wherein:
   the commonly used first optical-fiber-means segment includes just one optical fiber disposed to direct light from the light source to such fluid; and
   each respective second optical-fiber-means segment includes just one optical fiber, distinct from one another and distinct from the common optical fiber, disposed to direct liqht from such fluid to a respective detector.

6. The system of claim 1, wherein:
   the light-emitting means include at least two different light sources;
   the light-detecting means include one light detector used by both paths in common;
   the first optical-fiber-means segments of the two paths are distinct from one another, each directing light from a respective different one of the sources to such fluid; and
   one second optical-fiber-means segment is used by both paths in common.

7. The system of claim 6, wherein:
   the commonly used second optical-fiber-means segment includes just one optical fiber disposed to direct light from such fluid to the light detector; and
   each respective first optical-fiber-means segment includes just one respective optical fiber, disposed to direct light from a respective emitter to such fluid;
   the respective one optical fibers being distinct from one another and distinct from the common optical fiber.

8. The system of claim 1, also for use in measuring the chemical content of such fluid:
   wherein said light-emitting means emit light in a first particular wavelength band; and
   further comprising second light-emitting means that emit light in a second particular wavelength band;
   said first optical-fiber-means path segment also directing light in the second particular wavelength band from said second light-emitting means to such fluid;

said second optical-fiber-means path segment also directing light in the second particular wavelength band from such fluid to the receiving means; and said interpretation means also comparing light in the two wavelength bands received by the light-detecting means, to determine the chemical constituency of the fluid taking into account said determined quantity of corpuscles.

9. A system for determining the corpuscular content of a fluid that contains a varying quantity of corpuscles, comprising:

a light source that is remote from such fluid;

two light detectors that are both remote from such fluid;

a first optical fiber having a proximal end outside and remote from such fluid and disposed to receive light from the source, and having a distal end, from which the proximal end is remote, that is adapted to be juxtaposed to such fluid so as to project the light into such fluid;

second and third optical fibers, each having a distal end that is:

in fixed, known geometric relationship to the distal end of the first fiber, and adapted to be juxtaposed to such fluid to receive a respective portion of the light projected by the first fiber, after scattering by such fluid;

the second and third optical fibers also each having a proximal end that is remote from the respective distal end, and is outside and remote from such fluid, and is disposed to project its received portion of light to a respective one of the detectors;

the geometric relationships of the second and third optical-fiber distal ends with the first optical-fiber distal end being different from one another; and interpretation means for comparing the light projected to the two detectors to determine such quantity of corpuscles, taking into consideration said known geometric relationships between the distal ends of the fibers.

10. The system of claim 9, also for use in measuring the chemical content of such fluid:

wherein the light source emits light in a first particular wavelength band; and further comprising another light source that emits light in a second particular wavelength band;

the proximal end of the first optical fiber also receiving light in the second particular wavelength band from said other light source; and the distal end of the first optical fiber also projecting light in the second particular wavelength band from said other light source into such fluid; and the distal ends of the second and third optical fibers also receiving respective portions of the light in the second particular wavelength band projected from the first optical fiber, after scattering from such fluid; and the proximal ends of the second and third optical fibers also projecting their received portions of light in the second particular wavelength band to the respective detectors;

the interpretation means also comparing light in the two wavelength bands received by at least one of the two detectors, to determine the chemical constituency of the fluid taking into account said determined quantity of corpuscles.

11. The system of claim 9, wherein:

the geometrical relationship of the first and second optical-fiber distal ends being that they are substantially parallel and side-by-side;

the geometrical relationship of the first and third optical-fiber distal ends being that they are substantially parallel and separated from one another.

12. The system of claim 11:

also comprising a solid spacer element; and wherein the first and third optical-fiber distal ends are separated from one another by the second optical-fiber distal end and by the solid spacer element.

13. A system for determining the corpuscular content of a fluid that contains a varying quantity of corpuscles, comprising:

two light sources that are both remote from such fluid;

one light detector that is remote from such fluid;

a first optical fiber having a distal end adapted to be juxtaposed to such fluid so as to receive light scattered from such fluid, and having a proximal end that is remote from the distal end and is outside and remote from such fluid and disposed to project the received light to the remote detector;

second and third optical fibers, each:

having a proximal end outside and remote from such fluid and disposed to receive respective light from a respective one of the remote sources, and having a distal end, from which the respective proximal end is remote, that is in fixed, known geometric relationship to the distal end of the first fiber;

the distal ends of the second and third optical fibers being adapted for juxtaposition to such fluid to project into such fluid the light respectively received from the respective remote source;

the geometric relationships of the second and third optical-fiber distal ends with the first optical-fiber distal end being different from one another; and interpretation means for comparing the light projected to the remote detector to determine such quantity of corpuscles, taking into consideration said known geometric relationships between the distal ends of the fibers.

14. The system of claim 13, also for use in measuring the chemical content of such fluid:

wherein the light sources emit light in a first particular wavelength band; and further comprising other light sources that emit light in a second particular wavelength band;

the proximal ends of the second and third optical fibers also receiving respective light in the second particular wavelength band from the respective sources; and the distal ends of the second and third optical fibers also projecting respective light in the second particular wavelength band into such fluid;

the distal end of the first optical fiber also receiving light in the second particular wavelength band scattered from such fluid; and the proximal end of the first optical fiber also projecting light in the second particular wavelength band to the detector; and the interpretation means also comparing light in the two wavelength bands received by the detector, to determine the chemical constituency of the fluid taking into account said determined quantity of corpuscles.

15. The system of claim 13, wherein:

the geometrical relationship of the first and second optical-fiber distal ends being that they are substantially parallel and side-by-side;
the geometrical relationship of the first and third optical-fiber distal ends being that they are substantially parallel and separated from one another.

16. The system of claim 15:
also comprising a solid spacer element; and
wherein the first and third optical-fiber distal ends are separated from one another by the second optical-fiber distal end and by the solid spacer element.

* * * * *